US009428529B2

(12) United States Patent
Miller

(10) Patent No.: US 9,428,529 B2
(45) Date of Patent: Aug. 30, 2016

(54) PROCESS FOR PURIFICATION OF TRIVALENT PHOSPHOROUS LIGANDS THAT CAN BE USED FOR PREPARATION OF CATALYSTS

(75) Inventor: Glenn A. Miller, South Charleston, WV (US)

(73) Assignee: Dow Technology Investments LLC, Midland, MI (US)

( * ) Notice: Subject to any disclaimer, the term of this patent is extended or adjusted under 35 U.S.C. 154(b) by 28 days.

(21) Appl. No.: 14/345,489

(22) PCT Filed: Sep. 7, 2012

(86) PCT No.: PCT/US2012/054197
§ 371 (c)(1),
(2), (4) Date: Nov. 13, 2014

(87) PCT Pub. No.: WO2013/048701
PCT Pub. Date: Apr. 4, 2013

(65) Prior Publication Data
US 2015/0073169 A1    Mar. 12, 2015

Related U.S. Application Data

(60) Provisional application No. 61/541,291, filed on Sep. 30, 2011.

(51) Int. Cl.
| C07C 45/50 | (2006.01) |
| C07C 45/00 | (2006.01) |
| C07F 9/50 | (2006.01) |
| C07F 9/6574 | (2006.01) |
| B01J 31/18 | (2006.01) |

(52) U.S. Cl.
CPC ........ *C07F 9/65746* (2013.01); *B01J 31/1845* (2013.01); *B01J 2231/321* (2013.01)

(58) Field of Classification Search
CPC ........... B01J 2231/321; B01J 31/1845; C07F 9/65746
See application file for complete search history.

(56) References Cited

U.S. PATENT DOCUMENTS

| 3,527,809 | A | * | 9/1970 | Smith | C07C 45/49 502/162 |
| 3,706,822 | A | | 12/1972 | Caldwell et al. | |
| 4,143,075 | A | * | 3/1979 | Bryant | C07C 45/50 568/454 |
| 4,276,235 | A | | 6/1981 | McIsaac et al. | |
| 4,283,562 | A | | 8/1981 | Billig et al. | |
| 4,400,548 | A | | 8/1983 | Abatjoglou et al. | |
| 4,599,206 | A | | 7/1986 | Billig et al. | |
| 4,668,651 | A | | 5/1987 | Billig et al. | |
| 4,716,250 | A | * | 12/1987 | Abatjoglou | C07C 45/50 568/454 |
| 4,748,261 | A | * | 5/1988 | Billig | C07C 45/50 556/136 |
| 4,769,498 | A | | 9/1988 | Billig et al. | |
| 4,789,753 | A | | 12/1988 | Billig et al. | |
| 4,845,306 | A | * | 7/1989 | Puckette | B01J 31/04 556/136 |
| 5,235,113 | A | | 8/1993 | Sato et al. | |
| 5,710,344 | A | | 1/1998 | Breikss et al. | |
| 6,265,620 | B1 | | 7/2001 | Urata et al. | |
| 7,759,522 | B2 | | 7/2010 | Bright et al. | |
| 2003/0119923 | A1 | * | 6/2003 | Bohnen | B01J 31/2404 518/716 |
| 2004/0147785 | A1 | * | 7/2004 | Van Ginkel | C07F 1/02 568/17 |
| 2009/0171121 | A1 | | 7/2009 | Liu et al. | |

FOREIGN PATENT DOCUMENTS

WO    2009120210    10/2009

OTHER PUBLICATIONS

PCT/US2012/054197, Nov. 19, 2012, International Search Report and Written Opinion.
PCT/US2012/054197, Sep. 7, 2012, International Preliminary Report on Patentability.

* cited by examiner

*Primary Examiner* — Valerie Rodriguez-Garcia

(57) ABSTRACT

The present invention provides processes for purifying a trivalent phosphorous ligand that can be used for the preparation of catalysts for a hydroformylation process. In one embodiment, a process comprises: (A) contacting a trivalent phosphorous ligand, a contaminant metal, a first solvent, a polar complexing agent and a second solvent to form a mixture, (B) obtaining a first phase comprising the ligand and the first solvent, (C) obtaining a second phase comprising the second solvent and at least one complex of the contaminant metal and the polar complexing agent, and (D) separating the two phases prior to preparing a catalyst for use in a hydroformylation reactor.

9 Claims, No Drawings

PROCESS FOR PURIFICATION OF TRIVALENT PHOSPHOROUS LIGANDS THAT CAN BE USED FOR PREPARATION OF CATALYSTS

CROSS-REFERENCE TO RELATED APPLICATIONS

This application claims priority from provisional application Ser. No. 61/541,291, filed Sep. 30, 2011, which is incorporated herein by reference in its entirety.

BACKGROUND OF THE INVENTION

The invention relates to the purification of ligands that can be used for the preparation of catalysts.

Metal complex catalysts are a common class of catalysts and are used, for example, in commercial scale hydroformylation, hydrocyanation, olefin isomerization, cyclopropanation, and hydrogenation reactions. The presence of certain metals (primarily transition metals, e.g., iron) in hydroformylation systems is detrimental in that these contaminant metals can promote heavies formation or other side reactions.

The source of contaminant metals, such as iron, in trivalent phosphorous ligands can be from a variety of sources, such as reagents used in the production of the pendant groups during the coupling of phosphorous with the pendant groups, or corrosion of equipment during the production. One source of these metals is impurities in the ligands, such as triphenylphosphine and bisphosphites, supplied to the hydroformylation reactor. Nearly all preparations involve as the last step a coupling reaction of an R-M species with a halogen-phosphorous compound P-X as shown below:

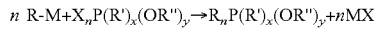

$n$ R-M+$X_n$P(R')$_x$(OR'')$_y$→$R_n$P(R')$_x$(OR'')$_y$+$n$MX where n+x+y=3 (assuming no polydendate moieties). Typically a water wash is used to remove the MX salts (typically M=Na, K, Li or Mg; X=Cl, Br). For example, the $R_n$P(R')$_x$(OR'')$_y$ is dissolved in a non-aqueous solvent such as toluene and the salts are removed by washing with water until the concentration of the dissolved halide, typically chloride, is sufficiently low indicating that the residual MX levels are low. The organic layer is decanted off and the resulting product is recrystallized or distilled as appropriate.

Since the ligands used in the hydroformylation reaction are good at complexing metals, they make it difficult to remove the iron without also removing the expensive catalytic metals, such as rhodium, from the hydroformylation reactor. U.S. Pat. No. 4,143,075 discloses a method for removing iron, but it involves shutting down the commercial production for the treatment.

It would be desirable to have a process for hydroformylation that did not require shutting down the production process to lower the level of iron in the reactor.

SUMMARY OF THE INVENTION

The invention is such a process, comprising:
(A) contacting a trivalent phosphorous ligand, a contaminant metal, a first solvent, a polar complexing agent and a second solvent to form a mixture
(B) obtaining a first phase comprising the ligand and the first solvent, and
(C) obtaining a second phase comprising the second solvent and at least one complex of the contaminant metal and the polar complexing agent,
(D) separating the two phases.

Surprisingly, very small amounts of the polar complexing agent can substantially remove unwanted contaminant metals from systems containing a very large excess of ligands that are known to be very good metal complexers.

DETAILED DESCRIPTION OF THE INVENTION

The process of the invention employs a ligand, an first solvent, a second solvent, and a polar complexing agent to remove a contaminant metal. In one embodiment of the invention, the metal is removed by an extraction process from the first solvent into the second solvent.

As used herein, "a," "an," "the," "at least one," and "one or more" are used interchangeably. The terms "comprises," "includes," and variations thereof do not have a limiting meaning where these terms appear in the description and claims. Thus, for example, an aqueous composition that includes particles of "a" hydrophobic polymer can be interpreted to mean that the composition includes particles of "one or more" hydrophobic polymers.

Also herein, the recitations of numerical ranges by endpoints include all numbers subsumed in that range (e.g., 1 to 5 includes 1, 1.5, 2, 2.75, 3, 3.80, 4, 5, etc.).

Also herein, the recitations of numerical ranges and/or numerical values, including such recitations in the claims, can be read to include the term "about." In such instances the term "about" refers to numerical ranges and/or numerical values that are substantially the same as those recited herein.

For the purposes of the invention, it is to be understood, consistent with what one of ordinary skill in the art would understand, that a numerical range is intended to include and support all possible subranges that are included in that range. For example, the range from 1 to 100 is intended to convey from 1.01 to 100, from 1 to 99.99, from 1.01 to 99.99, from 40 to 60, from 1 to 55, etc.

As used herein, the term "ppmw" means part per million by weight.

As used herein, the term "water soluble" means having a solubility in the second solvent (typically water) greater than 0.1wt % (at 25° C.).

In one embodiment of the invention, the process comprises contacting a solution of the ligand in the first solvent with a solution of the polar complexing agent in the second solvent, and allowing phase separation to simultaneously move the contaminant metals, and salts thereof, into the second solvent and away from the desired ligand product in the first solvent. Preferably, the polar complexing agent has virtually no solubility in the first solvent, so that the contaminant metals are removed from the first solvent, thus effectively removing them prior to subsequent purification steps. The process can be employed to rework off-spec material.

In one embodiment of the invention, the trivalent phosphorous ligand in a first solvent is contacted with a solid polar complexing agent, such as EDTA, for a period of time sufficient to remove the contaminant metal to the desired degree, followed by filtering away the solid polar complexing agent. In this embodiment, the solid polar complexing agent comprises adsorbed water, which acts as the second solvent.

The ligand can be any compound that will form a complex with a catalytic metal employed in hydroformylation or carbonylation reactions such as, for example, employed in the preparation of aldehydes by the hydroformylation process in which an alpha-olefin is hydroformylated with carbon monoxide and hydrogen in the presence of a rhodium catalyst.

The ligand advantageously is a phosphorous-containing ligand. In one embodiment of the invention, the phosphorous-containing ligand is a trivalent phosphorous ligand. Preferably, the ligand is not water soluble, i.e. less than 0.1 percent soluble by weight in water at 25° C. Examples of suitable ligands are disclosed in U.S. Pat. Nos. 4,283,562; 4,400,548; 4,599,206; 4,668,651; 4,748,261; 4,789,753; 5,235,113; 5,710,344; 6,265,620 and U.S. patent application publication 2009/0171121.

The function of the first solvent is to at least partially dissolve the ligand and enable the second solvent to contact the contaminant metal. The first solvent advantageously is not substantially miscible in the second solvent. The term "not substantially miscible" in this context means that the solubility of the first solvent in the second solvent does not exceed 10 wt. % at the temperature at which the extraction is conducted. Examples of first solvents include aromatic hydrocarbons (benzene, toluene, xylenes, ethylbenzene), saturated alkanes (hexane, octane), supercritical $CO_2$, higher molecular weight esters (such as pentylproprionate, butyl acetate, and dioctylphthalate), acetone derivatives such as dibutyl ketone and isophorone, with toluene being preferred. Mixtures of first solvents can be employed. The first solvent is used in an amount sufficient to dissolve most or all of the ligand at the extraction temperature. Advantageously, the extraction temperature is from 20° C. up to the lowest boiling point of the lowest boiling solvent of the first and second solvent. Advantageously, the amount of first solvent is sufficient to dissolve the ligand.

The function of the second solvent is to dissolve the complexing agent to enable it to contact the contaminant metal and form a polar metal-chelant complex which will preferentially stay in the second solvent. The second solvent advantageously is not substantially miscible in the first solvent. The term "not substantially miscible" in this context means that the solubility of the second solvent in the first solvent does not exceed 10 wt. % at the temperature at which the extraction is conducted. Examples of second solvents include water, methanol, dimethylsulfoxide, dimethylformamide, hexamethylphosphoramide, and mixtures thereof with water being preferred. The second solvent is used in an amount sufficient to (1) form a separate layer when mixed with the first solvent/ligand mixture and (2) dissolve the chelating agent. Typically the amount of polar chelating agent is very small, so that item (2) is usually not limiting. Generally, the amount of second solvent is equal to or as low as 10% of the first solvent (primarily limited by the ability to separate the layers in commercial operation).

The contaminant metal is an ionic/charged metal that is a Lewis acid catalyst for aldol condensations. More than one contaminant metal may be present. Examples of these metals include, but are not limited to, iron, nickel, chromium, tungsten, zinc, zirconium, titanium, and vanadium. The contaminant metal may be present in the form of a compound. In one embodiment of the invention, the initial concentration of contaminant metal in the ligand is from 100 to 10,000 ppmw, based on the weight of the ligand. Advantageously, the concentration can be reduced to less than 25 ppmw and preferably less than 10 ppmw, based on the weight of the ligand.

The polar complexing agent can be any material, other than a trivalent phosphorous compound, that forms a water-soluble chelate complex with the contaminant metal. The polar complexing agent is a sequestering agent that belongs to the general class of compounds called chelates. Chelates are multifunctional ligands having two or more sites for coordination with metal ions. Examples of the polar complexing agent include, without limitation, ethylenediamine tetraacetic acid (EDTA) and salts thereof. The amount of polar complexing agent employed advantageously is relatively small, e.g. from 1 to 500 times (molar equivalents) the amount of contaminant metal present. Preferably, the polar complexing agent has higher solubility in the second solvent compared to the first solvent. Advantageously, the ratio of the solubility of the polar complexing agent in the second solvent to the solubility of the polar complexing agent in the first solvent is at least 10:1, preferably 1000:1, and more preferably, at least 10,000:1. In one embodiment of the invention, the polar complexing agent is essentially insoluble in the first solvent.

Examples of polar complexing agents include: sodium salts of ethylenediamine tetraacetic acid ("EDTA") and related aminopolycarboxylic acids such as disodiumnitrilotriacetate, oxalic acid; malonic acid; cystene (2-amine-B-mercaptopropionic acid); tartaric acid; acetylacetone; citric acid; gluconic acid; nitrilotriacetic acid; N-2-hydroxyethyliminodiacetic acid; ethylenediamine-N,N-diacetic acid; 2'-hydroxy-pyridino(3':4'-2:3)pyrazine; 8-hydroxycinnoline; 8-hydroxyl-1,7-naphthyridine; ethylenediamine-N,N'-dipropionic acid; 8-hydroxyquinoline; 8-hydroxyquinoline-5-sulfonic acid; 2-hydroxycyclohexyliminodiacetic acid; 2,6-di(2-pyridyl)pyridine; ethylenediamine; diethylenetriamine; triethylenetetramine; B,B',B"-triaminotriethylamine; bipyridyl; 1,10-phenanthroline; 5-chloro-1,10-phenanthroline; 5-nitro-1,10-phenanthroline; 5-methyl-1,10-phenanthroline; 5-phenyl-1,10-phenanthroline; alanine; asparagine; glycine; methionine; phenylalanine; serine; tryptophan; valine; ethylenediamine tetrapropionic acid; salicylic acid; 5-sulfosalicylic acid; salicylaldehyde; benzoylacetone; benzoyltrifluoroacetone; dibenzoylmethane; 2-furoyl-benzoylmethane; 3,6-disulfo-1,8-dihydroxynaphthalene(chromotropic acid); 3,5-disulfopyrocatechol; 1,2-diaminocyclohexane, N,N,N'-tetracetic acid; Versene Fe-3 (tradename); methylaminediacetic acid; diethylenetriaminepentaacetic acid; ethylene glycol-bis-(B-aminoethylether)-N,N'-tetraacetic acid; ethyletherdiaminetetraacetic acid; N-hydroxyethylenediaminetriacetic acid; 1-methylethylenediaminetetraacetic acid (or 1,2-propylenediaminetetraacetic acid); N,N-dihydroxyethylglycine; ethylenediamine N,N,N',N'-tetrapropionic acid. For many of the above-described ligands, described in the protonated form, the alkali metal salts are preferred for purposes of the invention.

The concentration of polar complexing agent in the second phase comprising the second solvent is not critical. For total complexation of contaminant metal, one or more moles of polar complexing agent per mole of contaminant metal is employed.

The pH of the second phase comprising the second solvent can vary over a wide range without adversely affecting metal extraction. Since highly acidic or basic conditions enhance decomposition of ligands (particularly phosphites), it may be beneficial in certain instances to adjust the solution pH to a range of from about 3.5 to 10.

SPECIFIC EMBODIMENTS OF THE INVENTION

The following examples are given to illustrate the invention and should not be construed as limiting its scope. All parts and percentages are by weight unless otherwise indicated.

Comparative Experiment 1 (Not An Embodiment Of The Present Invention)

Preparation of 6,6'-(3,3',5,5'-tetra-tert-butylbiphenyl-2,2'-diyl)bis(oxy)didibenzo-[d,f][1,3,2]-dioxaphosphepine:

A crude bisphosphite is prepared as described in U.S. Pat. No. 4,769,498 and WO2009/120210 (A1). Using 623 parts 2,2'biphenol, 700 parts $PCl_3$ in 2000 parts toluene and 8 parts pyridine, a monochloridite is made. After removing excess $PCl_3$, 785 parts pyridine and 680 parts of 3,3',5,5'-tetra-tert-butyl-2,2'-biphenol (ISO-BHT, a bridging diol) in 3400 parts toluene are added. Samples taken from the resulting mixture are extracted with 1500 parts de-ionized water to remove pyridinium hydrochloride salt. The resulting crude product is then recrystallized from ethyl acetate. The resulting recrystallized product is analyzed for residual iron by atomic absorbance. The process using extraction with only water produces a product containing 47.2 ppm iron.

Example 2

Comparative Experiment 1 is repeated except that the extraction to remove pyridinium hydrochloride salt is done using 1500 parts 0.00875M EDTA-$Na_2$ in de-ionized water (to provide 2 equivalents of EDTA per iron). The process using extraction with aqueous EDTA produces a product containing 6.7 ppm iron.

Comparative Experiments 3 and 5 and Examples 4, 6 and 7

Two other batches of crude bisphosphite are prepared and evaluated according to the procedure of Comparative Experiment 1 and Example 2, except that different concentrations of EDTA are employed. The results are shown below.

| | Equivalents EDTA/Fe | Observed Fe Water only (ppm Fe) | Observed Fe Water workup with EDTA (ppm Fe) |
|---|---|---|---|
| Batch 2 | | | |
| Comparative Example 3* | — | 26 | |
| Example 4 | 7 | | BDL |
| Batch 3 | | | |
| Comparative Example 5* | — | 30.6 | |
| Example 6 | 0.5 | | 23 |
| Example 7 | 10 | | BDL |

(BDL = below detection limit, roughly 1 ppm)
*Not an embodiment of the invention

Example 8

A full commercial-scale batch of bisphosphite is treated as described above using 7 equivalents EDTA in water. The biphenol used in the preparation of the bisphosphite contains 25 ppm iron. The treatment of the crude bisphosphite gives a recrystallized product with only 7 ppm residual iron. The resulting material is tested in a hydroformylation reaction and its performance is indistinguishable from conventional non-EDTA treated material in regards to olefin conversion rate. A sample of the bisphosphite product is analyzed by attenuated total reflection (ATR) infrared spectroscopy. A comparison of the resulting spectra found no detectable amount of EDTA (based on the absence of a characteristic peak for EDTA at ~1620 $cm^{-1}$). This observation is confirmed by digitally subtracting the untreated reference spectrum from the EDTA treated sample spectrum. The resulting difference spectrum contains only noise. Based on this analysis, it is determined that EDTA is not present in the treated sample at levels detectable by infrared spectroscopy.

What is claimed is:

1. A process for purifying a trivalent organophosphorous ligand prior to forming metal complex catalysts for use in a hydroformylation process comprising:
   (A) contacting a non-water soluble trivalent organophosphorous ligand comprising a contaminant metal, a non-polar first solvent, a water soluble polar complexing agent and a polar second solvent to form a two phase mixture, with a first phase comprising the ligand and the first solvent and a second phase comprising the second solvent and at least one complex of the contaminant metal and the polar complexing agent; and
   (B) separating the two phases and obtaining the purified trivalent organophosphorous ligand from the first phase prior to forming a metal complex catalyst for use in a hydroformylation process,
   wherein the concentration of contaminant metal in the presence of the ligand prior to step (A), based on the weight of the ligand, is higher than the concentration of contaminant metal in the presence of the ligand in the first phase after step (B), based on the weight of the ligand, wherein the contaminant metal comprises at least one of iron, nickel, chromium, tungsten, zinc, zirconium, titanium, and vanadium, and wherein the concentration of each contaminant metal in the ligand in the first phase after step (B) is less than 25 ppmw, based on the weight of the ligand.

2. The process of claim 1 wherein the two phases are predominantly in the liquid phase.

3. The process of claim 1 wherein the second solvent comprises water.

4. The process of claim 1 wherein the contaminant metal comprises iron.

5. The process of claim 1 wherein the polar complexing agent comprises ethylenediamine tetraacetic acid and alkali metal salts thereof.

6. The process of claim 1 wherein the trivalent phosphorous ligand comprises at least one bisphosphite.

7. The process of claim 1 wherein the trivalent phosphorous ligand comprises at least one aryl or alkyl phosphine.

8. The process of claim 1, wherein the first solvent comprises an aromatic hydrocarbon, a saturated alkane, supercritical $CO_2$, pentylproprionate, butyl acetate, dioctylphthalate, acetone derivatives, and mixtures thereof.

9. The process of claim 1 wherein the trivalent phosphorous ligand comprises at least one bisphosphite, aryl phosphine, or alkyl phosphine, wherein the first solvent comprises an aromatic hydrocarbon, a saturated alkane, supercritical CO2, pentylproprionate, butyl acetate, dioctylphthalate, acetone derivatives, or mixtures thereof, wherein the second solvent comprises water, and wherein the polar metal complex comprises at least one of ethylenediamine tetraacetic acid, a sodium salt of ethylenediamine tetraacetic acid, disodiumnitrilotriacetate, oxalic acid, malonic acid, cystene (2-amine-B-mercaptopropionic acid), tartaric acid, acetylacetone, citric acid, gluconic acid, nitrilotriacetic acid, N-2-hydroxyethyliminodiacetic acid, ethylenediamine-N,N-diacetic acid, 2'-hydroxy-pyridino(3':4'-2:3)pyrazine, 8-hydroxycinnoline; 8-hydroxyl-1,7-naphthyridine, ethylenediamine-N,N'-dipropionic acid, 8-hydroxyquinoline, 8-hydroxyquinoline-5-sulfonic acid, 2-hydroxycyclohexyliminodiacetic acid, 2,6-di(2-pyridyl)pyridine, ethylenediamine, diethylenetriamine; triethylenetetramine, B,B',B''-triaminotriethylamine; bipyridyl, 1,10-phenanthroline, 5-chloro-1,10-phenanthroline, 5-nitro-1,10-phenanthroline, 5-methyl-1,10-phenanthroline, 5-phenyl-1,10-phenanthroline, alanine, asparagine, glycine, methionine, phenylalanine, serine, tryptophan, valine, ethylenediamine tetrapropionic acid, salicylic acid, 5-sulfosalicylic acid, salicylaldehyde, benzoylacetone, benzoyltrifluoroacetone, dibenzoylmethane, 2-furoyl-benzoylmethane, 3,6-disulfo-1,8-dihydroxynaphthalene(chromotropic acid), 3,5-disulfopyrocatechol, 1,2-diaminocyclohexane, N,N,N'-tetracetic acid, methylaminediacetic acid, diethylenetriaminepentaacetic acid, ethylene glycol-bis-(B-aminoethylether)-N,N'-tetraacetic acid, ethyletherdiaminetetraacetic acid, N-hydroxyethylenediaminetriacetic acid, 1-methylethylenediaminetetraacetic acid (or 1,2-propylenediaminetetraacetic acid), N,N-dihydroxyethylglycine, and ethylenediamine N,N,N',N'-tetrapropionic acid.

\* \* \* \* \*